US00PP34139P2

(12) United States Plant Patent
Ranney et al.

(10) Patent No.: US PP34,139 P2
(45) Date of Patent: Apr. 19, 2022

(54) ***FOTHERGILLA* PLANT NAMED 'NCFI1'**

(50) Latin Name: ***Fothergilla* x *intermedia***
Varietal Denomination: NCFI1

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/342,755

(22) Filed: Jun. 9, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

(56) References Cited

PUBLICATIONS https://plantoftheweek.com/2020/10/08/plant-of-the-week-legend-of-the-fall-bottlebrush/; Oct. 8, 2020; 2 pages.*
https://www.provenwinners.com/plants/fothergilla/legend-small-bottlebrush-fothergilla-x-intermedia; Jul. 31, 2021; 3 pages.*

* cited by examiner

*Primary Examiner* — Kent L Bell
(74) *Attorney, Agent, or Firm* — Cassandra Bright

(57) ABSTRACT

A new and distinct cultivar of *Fothergilla* plant named 'NCFI1' with a compact plant habit, large, showy, fragrant white flowers and brilliant fall foliage colors. The new variety of *Fothergilla* is suitable for ornamental horticultural purposes.

3 Drawing Sheets

Latin name of the genus and species: *Fothergilla* x *intermedia.*

Variety denomination: 'NCFI1'.

BACKGROUND OF THE INVENTION

The present invention comprises a new and distinct *Fothergilla* cultivar hereinafter referred to by the cultivar name 'NCFI1'. This new *Fothergilla* was developed through a breeding program at Mills River, N.C. 'NCFI1' was selected from a population of seedlings derived from open-pollinated *Fothergilla* x *intermedia.* The first asexual propagation of 'NCFI1' was carried out in July 2010 by rooting stem cuttings at a research greenhouse in Mills River, N.C. and has been asexually reproduced repeatedly by vegetative cuttings over an 11-year period. 'NCFI1' roots readily from softwood cuttings treated with a basal dip of 3,000-4,000 ppm indole butyric acid (potassium salt) in water. 'NCFI1' has been found to retain its distinctive characteristics through successive asexual propagations.

SUMMARY OF THE INVENTION

The following are the unique combination of characteristics of this new cultivar when grown under standard horticultural practices at a research nursery in Mills River, N.C.

1. A dwarf habit with dense branching.
2. Abundant, showy white flowers in spring.

3. Bluish-green summer foliage with attractive multi-colored fall foliage color.

COMPARISON WITH PARENT VARIETIES

Records of the parent variety characteristics are not available. The inventor cannot make a comparison to the seed parent. The pollen parent is unknown.

COMPARISON WITH COMMERCIAL CULTIVARS

'NCFI1' is distinguished from *Fothergilla* x *intermedia* 'Alice' U.S. Plant Pat. No. 32,049 in that 'NCFI1' has a smaller more compact habit. 'NCFI1' grows to 60-70 cm tall whereas 'Alice' grows to 120-150 cm tall. 'NCFI1' is further distinguished from 'Alice' in that 'NCFI1' has larger inflorescences of an average of 6.2 cm in length, whereas 'Alice' has inflorescences of 3.5 cm in length. 'NCFI1' is distinguished from *Fothergilla* x *intermedia* 'Mt. Airy' (unpatented) in that 'Mt. Airy' grows to 180 cm tall and 'NCFI1' is less than half its size.

BRIEF DESCRIPTION OF THE DRAWINGS

This new *Fothergilla* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Fothergilla*. Plants photographed are approximately 2 years of age.

DETAILED BOTANICAL DESCRIPTION

Figure 1:
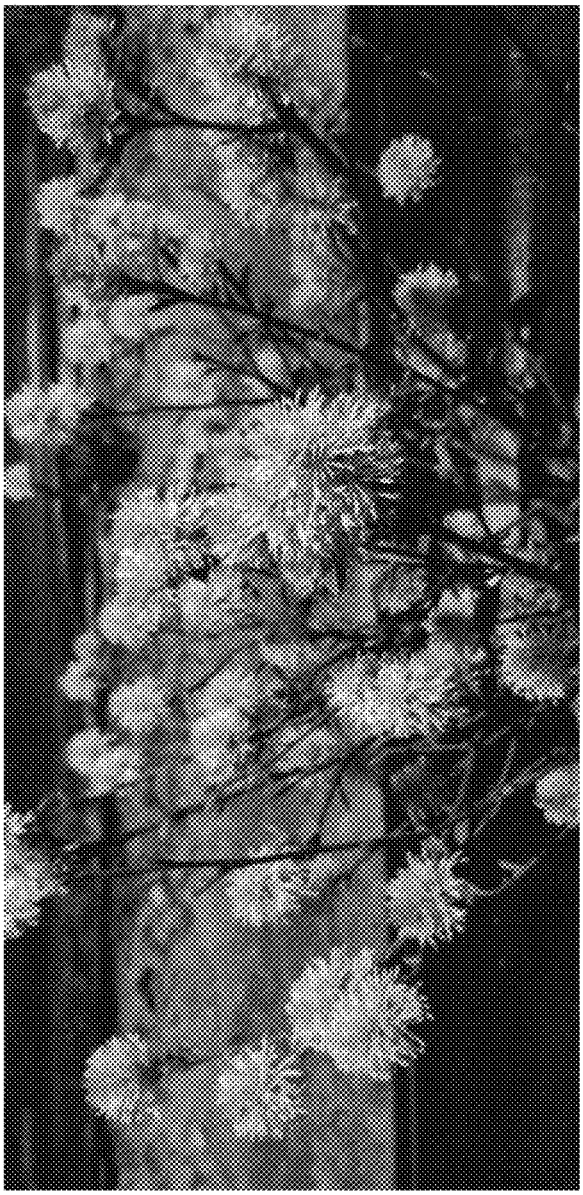
FIG. 1 is a photograph showing inflorescences of 'NCFI1' taken on Apr. 12, 2015 in Mills River, N.C.
Figure 2:
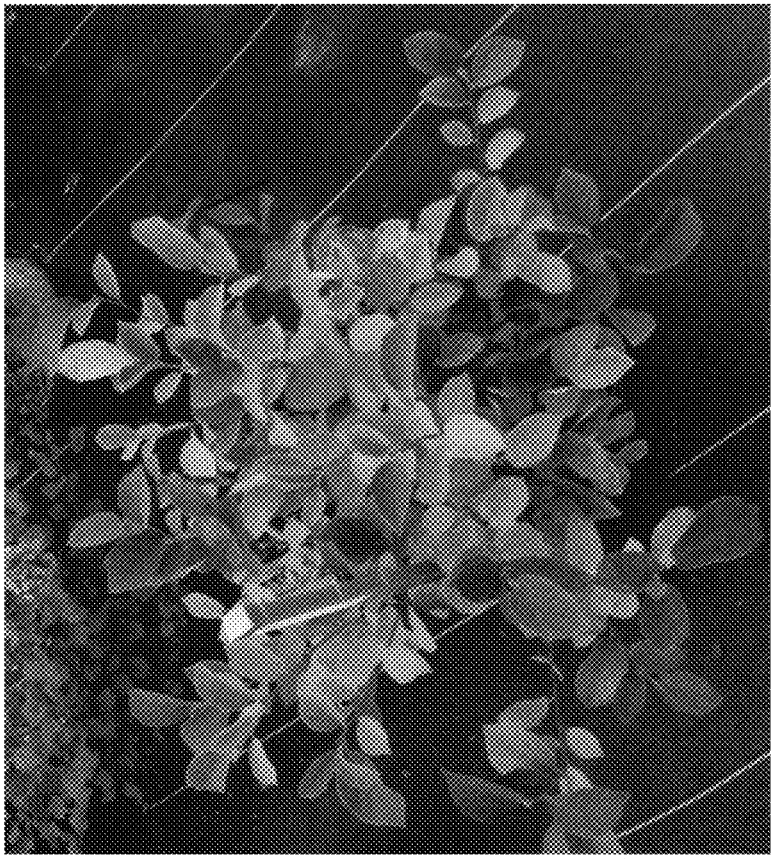
FIG. 2 is a photograph showing the fall foliage color of 'NCFI1' taken on Oct. 15, 2019, in Grand Haven, Mich.
Figure 3:
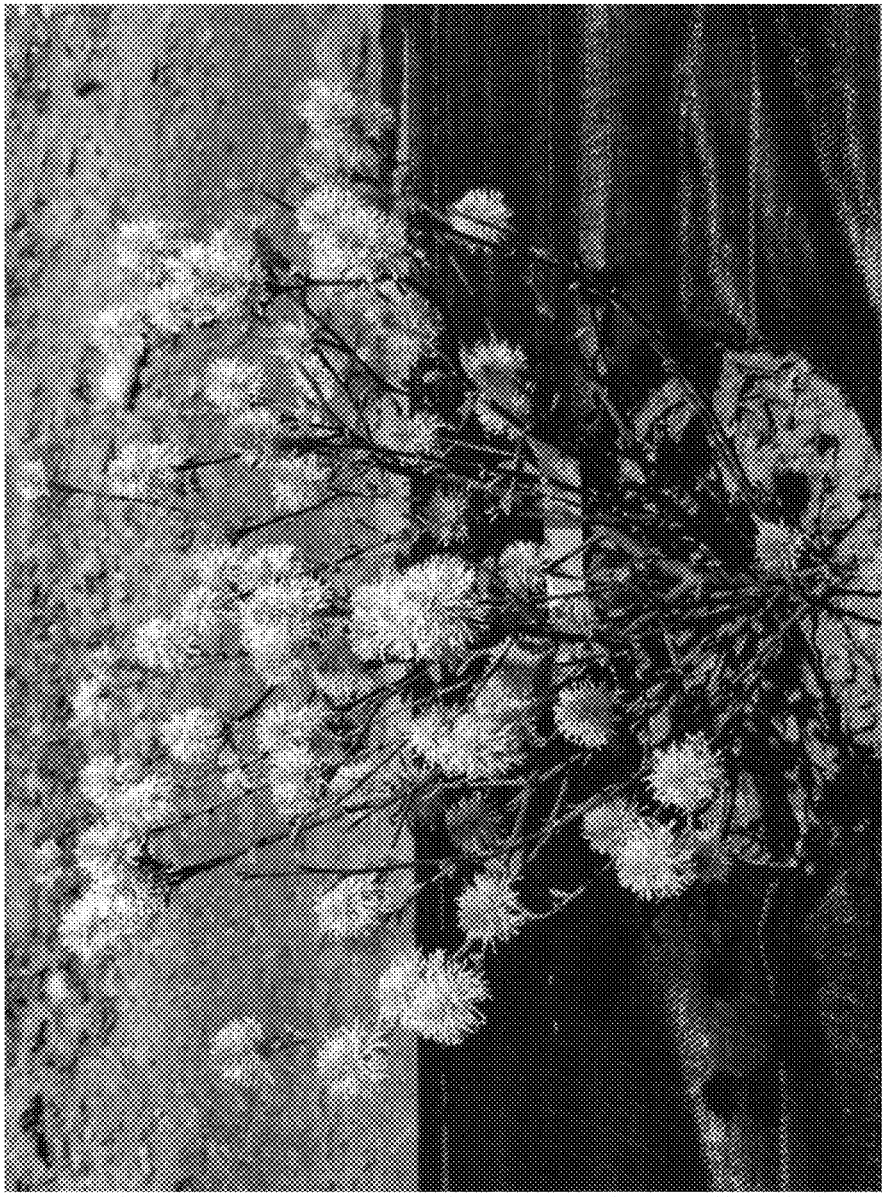
FIG. 3 is a photograph showing the habit and inflorescences of a field-grown 'NCFI1' taken on Apr. 12, 2015 in Mills River, N.C.

The following is a detailed description of the botanical characteristics of the new and distinct *Fothergilla* cultivar known by the denomination 'NCFI1'. The detailed description was taken on a five-year-old field-grown plant in Mills River, N.C. in 2020. All colors cited herein refer to The Royal Horticultural Society Colour Chart (The Royal Horticultural Society (RHS), London, Sixth Edition). Where specific dimensions, sizes, colors, and other characteristics are given, it is to be understood that such characteristics are approximations or averages set forth as accurately as practicable.

Plant:

*Growth habit.*—Dwarf, rounded habit.

*Height.*—60-70 cm.

*Width.*—60-80 cm.

*Shoots and branches.*—

*Shoots* (*current year's growth*).—Color: Grey-Brown (199A). Texture: Pubescent.

*Shoots* (*prior year's growth*).—Color: Grey-Brown (N199C). Texture: Glabrous, with vertical fissures of Grey (201C).

*Branches* (woody branches 2-4 *years old*).—Branch length: Avg. 38 cm (Range 20 to 55 cm). Branch diameter: Avg. 0.3 cm (0.15 to 0.6 cm). Color: Grey-Brown (N199C). Texture: Glabrous, with vertical fissures of Grey (201C).

*Internode length.*—Avg. 2.8 cm (0.5 to 4.5 cm).

Foliage:

*Type.*—Simple.

*Persistence.*—Deciduous.

*Arrangement.*—Alternate.

*Shape.*—Broad elliptical.

*Length of lamina.*—Avg. 5.3 cm (3.2 to 9 cm).

*Width of lamina.*—Avg. 3.7 cm (2.3 to 6.5 cm).

*Emerging leaves.*—Color: Upper: Yellow-Green (144A). Lower: Yellow-Green (146A). Texture: Pubescent.

*Mature leaves during growing season.*—Color: Upper: Green (137B). Lower: Green (137D). Fall foliage color: A range of colors including Brilliant Yellow (9C), Greyed-Orange (163B), Red (46A) and Greyed-Purple (187A).

*Apex.*—Acute.

*Base.*—Symmetrical, cuneate-cordate.

*Margin.*—Serrate-sinuate.

*Texture.*—Pubescent all surfaces.

*Venation.*—Pinnate.

*Vein color.*—Upper: Greyed-Green (195B). Lower: Greyed-Green (195B).

*Leaf attachment.*—Petiolate.

*Petiole.*—Length: Avg. 0.5 cm (0.4 to 0.7 cm). Diameter: About 0.1 cm. Color: Greyed-Green (195B). Texture: Pubescent.

Inflorescence:

*Description.*—Terminal spikes of brush-like, apetalous flowers.

*Number of inflorescences per plant.*—About 100.

*Number flowers per inflorescence.*—About 23.

*Flowering season.*—Late March to Mid-April in Mills River, N.C.

*Fragrance.*—Fragrant.

*Inflorescence.*—Length: About 6.2 cm (4.8 to 6.8 cm). Diameter: About 3.5 cm (2.5 to 4.0 cm).

*Flower.*—Length: Avg. 1.5 cm (1.2 to 1.7 cm). Diameter: Avg. 1.4 cm (1.0 to 1.7 cm). Depth: Avg. 1.5 cm.

*Bud.*—Shape: Oblong. Length: Avg 0.8 cm (0.6 to 1.0 cm). Diameter: About 0.6 cm. Color: Yellow-Green (144B) with bracts of Grey-Brown (199B).

*Petals.*—None.

*Sepal.*—Inconspicuous and minute.

*Peduncle.*—Length: About 5.0 cm. Diameter: About 0.3 cm. Color: Yellow-Green (144A). Texture: Pubescent.

Reproductive organs:

*Gynoecium.*—Pistil number: 1. Pistil length: About 1.2 cm. Stigma shape: Linear. Stigma color: White (155B). Style number: 2. Style length: About 1 cm. Style color: White (155B).

*Androecium.*—Stamen number: Avg. 18 (14-20). Filament length: Avg 1.0 cm (0.8 to 1.2 cm). Filament diameter: About 0.1 cm at apex, tapering to base. Filament color: White (155C). Anther shape: Bilobed. Anther size: Less than 0.1 cm. Anther color: Yellow-Orange (22A). Amount of pollen: Average. Pollen color: Yellow-Orange (22A).

Other characteristics:

*Fruit and seed.*—None observed.

*Disease and insect resistance.*—No significant disease or insect pests have been observed.

*Cold hardiness.*—At least USDA zone 6b; testing has not been completed in colder zones.

What is claimed is:

1. A new and distinct cultivar of *Fothergilla* plant named 'NCFI1' as illustrated and described herein.

* * * * *